United States Patent [19]

Mann

[11] 4,180,879
[45] Jan. 1, 1980

[54] BODY POSITIONER

[76] Inventor: Rose A. Mann, 1368 Pleasant, St. Paul, Minn. 55102

[21] Appl. No.: 930,990

[22] Filed: Aug. 4, 1978

[51] Int. Cl.² .............................................. A61G 7/10
[52] U.S. Cl. .................................... 5/508; 2/69; 128/134
[58] Field of Search ................ 5/61, 82 R, 91, 92, 5/317 R, 327 R, 336; 128/75, 134; 2/48, 69, 69.5; 297/384

[56] References Cited

U.S. PATENT DOCUMENTS

| | | |
|---|---|---|
| 3,093,829 | 6/1963 | Maine .......................................... 2/48 |
| 3,259,126 | 7/1966 | Greiert ...................................... 2/69.5 |
| 3,458,878 | 8/1969 | Combs ........................................ 5/92 |
| 3,535,718 | 10/1970 | Murcott ..................................... 5/336 |
| 3,801,986 | 4/1974 | Purdon ........................................ 2/69 |
| 3,884,225 | 5/1975 | Witter ........................................ 5/92 |

*Primary Examiner*—Casmir A. Nunberg
*Attorney, Agent, or Firm*—Jacobson and Johnson

[57] ABSTRACT

A body positioner for turning and holding a person lying on a bed with the body positioner comprising a shaped body sheet having members extending therefrom for engaging the side rails of a bed. The members including dual fastening means for preventing the patient from accidentally releasing the body positioner.

10 Claims, 4 Drawing Figures

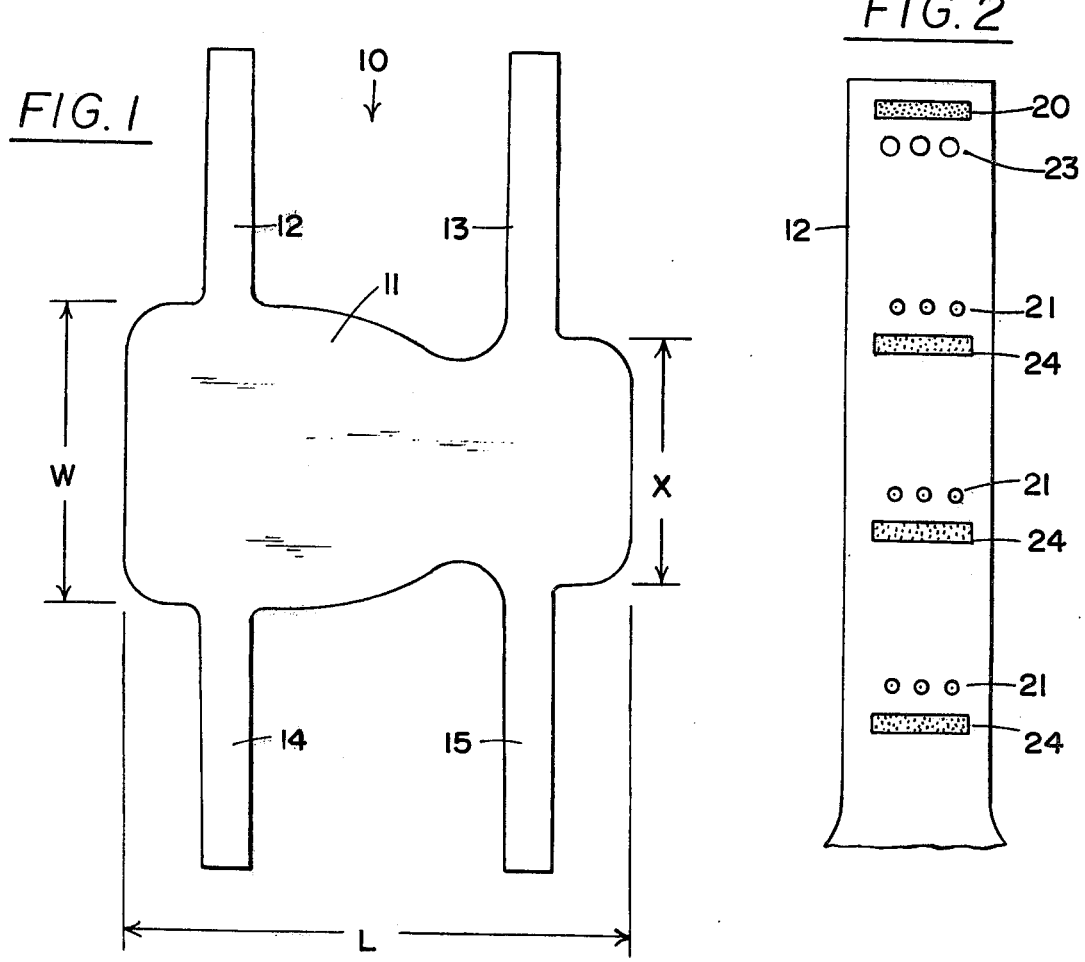
FIG. 1
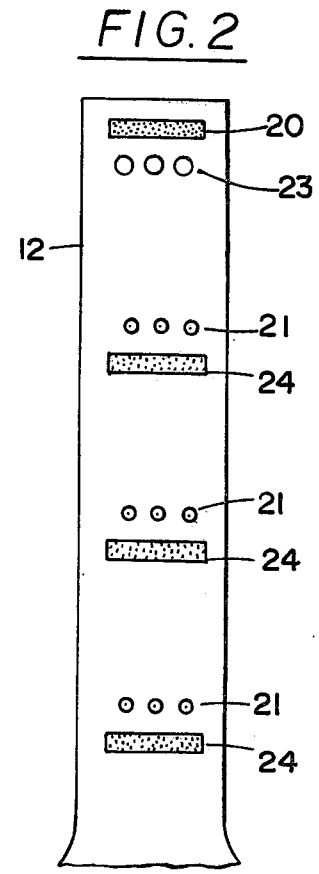
FIG. 2
FIG. 3
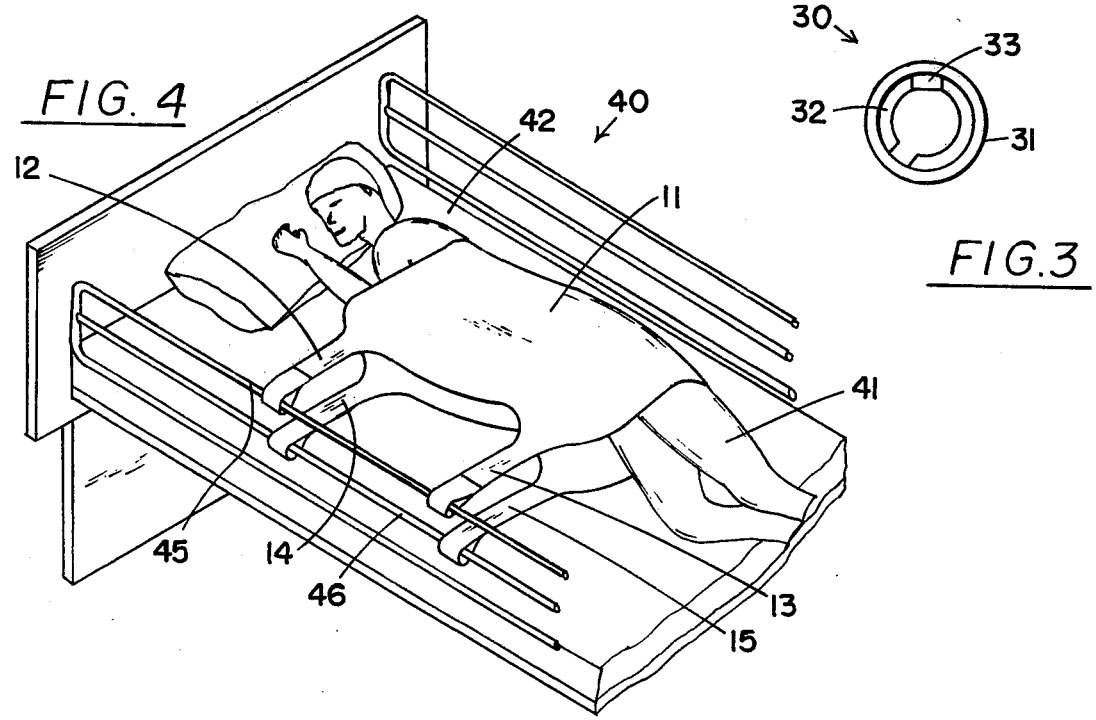
FIG. 4

BODY POSITIONER

BACKGROUND OF INVENTION

1. Field of the Invention

This invention relates generally to health aid devices and, more specifically, to a body positioner for holding a patient in a proper position.

2. Description of the Prior Art

Briefly, the concept of restraining and holding devices for patients is well known in the art. Some of the prior art devices are for the purpose of supporting patients who are unable to support themselves in a chair. For example, the Posey U.S. Pat. No. 2,851,033 shows a supporting means for securing invalids to a chair. The Posey patent has a body portion and straps connected thereto that fasten to a chair bottom and back.

The Shirrod U.S. Pat. No. 3,182,338 shows a belt which attaches to the bed frame and around the patients waist to restrain a person lying in bed.

The Gaylord U.S. Pat. No. 3,474,781 shows a restraining device for a bedridden person. The Gaylord restraining device has sections that extend across and under the person's body. A portion of the sections fasten around the person's waist to restrain the person in the bed.

The Higdon U.S. Pat. No. 1,334,901 shows a turning pad used for turning a patient lying in bed. The pad has wide ends for grasping by the user.

The Edelin U.S. Pat. No. 1,063,423 shows a backrest for a bed patient. The backrest has a series of loops for engaging the arms of a person so that the person can sit in an upright position in a bed.

In hospitals and nursing homes, patients who are seriously ill or invalids require frequent turning to prevent painful bedsores from developing on their body. In order to turn a patient on their side it is usually necessary to support the patient so the patient does not accidentally roll back. The Witter U.S. Pat. No. 3,884,225 shows such a device to support a patient. Witter uses a flexible muzlin sheet having a fleece cushion. Attachment members located at the ends fasten to the bed rail to hold the bedridden person. The attachment members may be flexible straps which are looped around the bed rail and fastened to the opposite side of the sheet. The prior art Witter device contains a fleece lining and is substantially rectangular in shape for fastening around a portion of the patients body. The present invention, in contrast to the prior art, provides a body positioner that comfortably supports the upper torso of the patient. In addition, the body positioner has a special shape that allows the body positioner to be used with male or female patients. Dual fasteners prevent the patient from aggravating his or her condition as the fasteners cannot be accidentally loosened. For sanitary purposes, the body positioner is made of washable material so that it can be readily cleaned.

BRIEF DESCRIPTION OF THE DRAWINGS

FIG. 1 shows a plane view of the positioner;

FIG. 2 shows an enlarged view of the fastening members located on the body positioner;

FIG. 3 shows a single fastener; and

FIG. 4 shows a body positioner supporting a patient in a side position.

SUMMARY OF THE INVENTION

Briefly, the present invention comprises a lightweight body positioner having a contoured shape and length which comfortably supports either a male or female bed patient. Connecting straps having dual fasteners prevent accidental loosening of the body positioner.

DESCRIPTION OF THE PREFERRED EMBODIMENT

Referring to FIG. 1 reference numeral 10 designates a body positioner 10 having a contoured body shape with a length L, a first width W and a second width X. Fastening straps are denoted by reference numerals 12, 13, 14, and 15. Note, dimension W is substanstially larger than dimension X. The length, which is designated by L, is sufficiently long so as to extend the entire length of a patients torso while the first width, which is designated by dimension W, is sufficiently wide so as to extend around the largest portion of the patients torso. The second width, which is designated by dimension X, is sufficiently large so as to extend around the smaller portion of the patients torso. The contoured shaped body positioner in which one portion has a wider dimension than the other provides a comfortable body positioner for use with either male or female patients. Generally, male patients have a shoulder area that is larger than their hips, whereas a female patient has a shoulder area which is smaller than her hips. Consequently, with a male patient the wider portion (W) having fasteners 12 and 14 is placed towards the head of the user and the narrow portion (X) toward the hips for the user. For female patients the narrow portion (X) is placed around the shoulder area and the wider portion (W) around the hips.

Referring to FIG. 2, reference numeral 20 designates strap 12 having a female fabric fastener 20 and a row of female snaps 23. Fabric fastener 20 comprises strands of material that engage or catch on outwardly protecting strands of material. These types of fasteners are commercially available and sold under the tradename Velcro fasteners. Located below fasteners 20 and 23 are identical sets of fasteners which are identified by reference numerals 21 and 24. The purpose of these sets of fasteners is to provide adjustment in fastening fasteners 20 and 23 thereto. In operation, fastener 20 may engage the adjacent fastener 24 or any other fastener 24.

The purpose of having a dual fastener is to provide a secure fastening that prevents the patient from accidentally losing the strap. If the patient should accidentally loosen a strap, it would release the support to the patients torso, which may aggravate the injury of any injured person or make an ill person very uncomfortable.

Referring to FIG. 3 reference numeral 30 designates a one-way snap having an outside section 31 with a snap ring 32 located therein. A ridge 33 located therein acts as a guide and coacts with the male snap (not shown) to prevent the opening of snap unless the two portions of the snap are properly positioned with respect to each other. Typically, such one-way snaps are well known in the art. The use of a one-way snap in addition to a plurality of straps virtually assures the patient does not accidentally loosen a strap yet can be opened at all times.

Referring to FIG. 4, reference numeral 40 designates a patient using my body positioner. Reference numeral 41 designates a patient laying in bed 42 having a body positioner 11 thereon. Note, body positioner straps 12 and 13 fastens to a top rail 45 and straps 14 and 15 fasten to middle rail 46. The straps and positioner coact to hold a patient in a side position so that the patient does not roll backwards. Temporarily supporting a patient on the side prevents the patient from getting bedsores, particularly, those invalids who cannot move their body and would develop bedsores if they were allowed to lay in one position for an extended period of time. FIG. 4 shows male patient support with the wider portion of the body positioner near the shoulders of the patient. With a female patient body positioner 11 would be reversed with straps 13 and 15 extending from the shoulder area and straps 12 and 14 extending from the hip area. For the patients comfort and sanitary purposes, body positioner 11 is made from lightweight fabric material such as drill fabric.

In addition to providing support for the entire torso of the patient, my body positioner may also be used when one must "lamp" a person. That is, often times it is necessary to direct a heat lamp at a patients back. To do so, my body positioner provides sufficient support so that either the lower or upper straps could be disengaged from the rail and folded back. For example, if the upper torso of the patient required "lamping" only the bottom fasteners and straps would be used to support the patient. Obviously, such use is limited to short periods of time as extended support with only half of my body positioner may become uncomfortable after a period of time.

I claim:

1. A body positioner for holding a person lying on a bed having a rail, said body positioner comprising a sheet of material having a length equal to or greater than the torso length of the person lying on the bed, said body positioner having a first section of width W and a second section of width X, the width W sufficiently large so that the said first section is operable for encompassing the larger portion of the torso of a patient lying on the bed, said width X being less than the width W but sufficiently large to encompass the smaller portion of the torso of a person lying on a bed, said body positioner reversible so that if a patient has a smaller upper torso, said section of width X can be placed around the upper torso of the patient, but if a patient has a larger upper torso, said section of width X can be placed around the upper torso of the patient, and means for securing said body positioner to the rail of a bed.

2. The invention of claim 1 when said means includes a plurality of straps extending from said body positioner.

3. The invention of claim 2 when said straps include a snap fastener for attaching said straps to a rail.

4. The invention of claim 3 when said straps include fabric fasteners for preventing accidental release of said straps.

5. The invention of claim 4 when said straps include a plurality of fastening members.

6. The invention of claim 5 when said snap fastener is openable in a single direction.

7. The invention of claim 6 wherein each of said straps includes at least three sets of fasteners.

8. The invention of claim 7 wherein said body positioner comprises fabric material.

9. The invention of claim 8 wherein said body positioners and said straps form a one-piece body positioner.

10. The invention of claim 9 wherein said straps on said body positioner includes at least a plurality of fasteners for positionable attachment of said straps to the rail.

* * * * *